US012544132B2

(12) United States Patent
Brannan

(10) Patent No.: US 12,544,132 B2
(45) Date of Patent: Feb. 10, 2026

(54) DC BLOCK PATIENT ISOLATOR FOR A MICROWAVE GENERATOR

(71) Applicant: Covidien LP, Mansfield, MA (US)

(72) Inventor: Joseph D. Brannan, Lyons, CO (US)

(73) Assignee: Covidien LP, Mansfield, MA (US)

( * ) Notice: Subject to any disclaimer, the term of this patent is extended or adjusted under 35 U.S.C. 154(b) by 799 days.

(21) Appl. No.: 17/765,855

(22) PCT Filed: Sep. 3, 2020

(86) PCT No.: PCT/US2020/049100

§ 371 (c)(1),
(2) Date: Apr. 1, 2022

(87) PCT Pub. No.: WO2021/091612

PCT Pub. Date: May 14, 2021

(65) Prior Publication Data

US 2022/0323151 A1 Oct. 13, 2022

Related U.S. Application Data

(60) Provisional application No. 62/933,199, filed on Nov. 8, 2019.

(51) Int. Cl.
*A61B 18/18* (2006.01)
*A61B 18/00* (2006.01)

(52) U.S. Cl.
CPC ..................... *A61B 18/1815* (2013.01); *A61B 2018/00642* (2013.01); *A61B 2018/00702* (2013.01);

(Continued)

(58) Field of Classification Search
CPC ...... A61B 18/1815; A61B 2018/00642; A61B 2018/00702; A61B 2018/00815; A61B 2018/00821; A61B 2018/1823
See application file for complete search history.

(56) References Cited

U.S. PATENT DOCUMENTS 6,207,901 B1 * 3/2001 Smith ...................... H01P 1/30 174/102 R
2005/0264381 A1 12/2005 Grothen et al.

(Continued)

FOREIGN PATENT DOCUMENTS

CN 104812323 A 7/2015
CN 109069202 A 12/2018

(Continued)

OTHER PUBLICATIONS

European Examination Report issued in corresponding application EP 20772180.4 dated Nov. 15, 2024 (4 pages).

(Continued)

*Primary Examiner* — Joseph A Stoklosa
*Assistant Examiner* — Annie L Shoulders
(74) *Attorney, Agent, or Firm* — Carter, DeLuca & Farrell, LLP

(57) ABSTRACT

A patient isolator for a microwave generator includes a DC block grounded to a microwave module of the microwave generator, a proximal absorber wrapped around a proximal portion of the DC block, and a distal absorber wrapped around a distal portion of the DC block and separated from the proximal absorber by a gap.

9 Claims, 11 Drawing Sheets

(52) U.S. Cl.
CPC ............... *A61B 2018/00815* (2013.01); *A61B 2018/00821* (2013.01); *A61B 2018/1823* (2013.01)

(56) References Cited

U.S. PATENT DOCUMENTS

| | | | | |
|---|---|---|---|---|
| 2012/0243823 | A1* | 9/2012 | Giboney | H01P 1/162 385/14 |
| 2017/0056106 | A1 | 3/2017 | Mcerlean et al. | |
| 2022/0190453 | A1* | 6/2022 | Beale | A61B 18/1815 |
| 2022/0202490 | A1* | 6/2022 | Hancock | A61B 8/12 |

FOREIGN PATENT DOCUMENTS

| | | | |
|---|---|---|---|
| JP | 2015530172 | A | 10/2015 |
| JP | 2016119416 | A | 6/2016 |
| WO | 2014049332 | A1 | 4/2014 |
| WO | 2020193646 | A1 | 10/2020 |

OTHER PUBLICATIONS

Japanese Office Action issued in corresponding application JP 2022-526092 mailed Mar. 29, 2024, together with English language translation (7 pages).
International Search Report and Written Opinion of the International Searching Authority issued in corresponding application PCT/US2020/049100 mailed Nov. 12, 2020 (12 pages).
Office Action issued in corresponding Chinese application No. 202080083042.X mailed May 27, 2025, together with English language translation retrieved from the Global Dossier.

* cited by examiner

DC BLOCK PATIENT ISOLATOR FOR A MICROWAVE GENERATOR

CROSS-REFERENCE TO RELATED APPLICATIONS

This application is a U.S. National Stage Application filed under 35 U.S.C. § 371 (a) of International Patent Application No. PCT/US2020/049100, filed Sep. 3, 2020, which claims the benefit of and priority to U.S. Provisional Patent Application Ser. No. 62/933,199, filed on Nov. 8, 2019, the entire contents of which is being incorporated by reference herein

INTRODUCTION

The present disclosure relates to microwave generators and, more specifically, to a DC block isolator of a microwave generator for patient isolation.

BACKGROUND

In microwave ablation, an electromagnetic field is used to heat and destroy tumor cells. Treatment may involve inserting an ablation probe into tissues where cancerous tumors have been identified. Once the ablation probe is properly positioned, the ablation probe induces an electromagnetic field within the tissue surrounding the ablation probe to ablate the tissue.

Typically, systems for microwave ablation procedures include a microwave generator and a microwave instrument such as an ablation probe having an antenna assembly. The microwave generator and microwave instrument are operatively coupled to each other by a coaxial cable for carrying microwave signals from the microwave generator to the microwave instrument. Microwave generators typically include circuitry for generating microwave signals and a controller for controlling the operation of the circuitry and controlling a user interface, such as a display. The user interface includes user controls for setting characteristics of the microwave signals, such as buttons for adjusting the power level of the microwave signals.

Some microwave generators may incorporate patient isolators for electrically isolating the patient from components of the microwave generator. DC block patient isolators operate with capacitive gaps across breaks in inner and outer conductors of a coaxial waveguide. Low frequency signals see this coupling as high impedance, whereas an operational frequency of 2.45 GHz sees this coupling as low impedance. However, the breaks in the outer conductor of the coaxial line within the DC block allow for unwanted radiation of high frequency energy outside the waveguide, thereby causing interference to other components of the microwave generator. In certain instances, the unwanted radiation imposes interference on sensor signals, the accuracy of which is integral to the proper control and operation of the microwave generator.

SUMMARY

In accordance with aspects of the present disclosure, a patient isolator for a microwave generator is provided. The patient isolator for a microwave generator includes a DC block configured to be grounded to a microwave module of the microwave generator, a proximal absorber wrapped around a proximal portion of the DC block, and a distal absorber wrapped around a distal portion of the DC block and separated from the proximal absorber by a gap.

In an aspect, the gap separating the proximal and distal absorbers is about a 6 mm gap.

The DC block may include a proximal mounting block and a distal mounting block. In an aspect, the proximal mounting block is conductive and the DC block is grounded to the microwave module of the microwave generator via the proximal mounting block.

In an aspect, at least one of the proximal absorber or the distal absorber is a high loss cavity resonance absorber.

In accordance with another aspect of the present disclosure, a microwave generator is provided. The microwave generator includes a microwave module configured to deliver a microwave signal to a microwave instrument coupled to the microwave generator, a generator controller in communication with the microwave module, the generator controller configured to control the microwave module, and a patient isolator coupled to the microwave module. The patient isolator includes a DC block grounded to the microwave module, a proximal absorber wrapped around a proximal portion of the DC block, and a distal absorber wrapped around a distal portion of the DC block and separated from the proximal absorber by a gap.

In an aspect, the gap separating the proximal and distal absorbers is about a 6 mm gap.

The DC block may include a proximal mounting block and a distal mounting block. In an aspect, the proximal mounting block is conductive and the DC block is grounded to the microwave module of the microwave generator via the proximal mounting block.

In an aspect, at least one of the proximal absorber or the distal absorber is a high loss cavity resonance absorber.

In accordance with another aspect of the present disclosure, an ablation system is provided and includes a microwave instrument configured to delivery microwave energy to tissue and a microwave generator configured to couple to the microwave instrument. The microwave generator includes a microwave module configured to deliver a microwave signal to the microwave instrument, a generator controller in communication with the microwave module, and a patient isolator coupled to the microwave module. The patient isolator includes a DC block grounded to the microwave module of a microwave generator, a proximal absorber wrapped around a proximal portion of the DC block, and a distal absorber wrapped around a distal portion of the DC block and separated from the proximal absorber by a gap.

In an aspect, the gap separating the proximal and distal absorbers is about a 6 mm gap.

The DC block may include a proximal mounting block and a distal mounting block. In an aspect, the proximal mounting block is conductive and the DC block is grounded to the microwave module of the microwave generator via the proximal mounting block.

In an aspect, at least one of the proximal absorber or the distal absorber is a high loss cavity resonance absorber.

BRIEF DESCRIPTION OF THE DRAWINGS

Various embodiments of the present disclosure are described herein with reference to the drawings wherein.

DETAILED DESCRIPTION

Particular embodiments of the present disclosure are described below with reference to the accompanying drawings. In the following description, well-known functions or constructions are not described in detail to avoid obscuring the present disclosure in unnecessary detail.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

Microwave generators may perform several functions in addition to and relating to the main function of generating a microwave signal to be used by a microwave instrument. While additional features add utility to a microwave generator, they also require more power, use more processing resources, and add to the overall cost of manufacturing. The present disclosure relates to a modular microwave generator system that includes physical modules and components with decentralized and isolated processing to perform auxiliary functions associated with the microwave generator. One such component is an improved DC block patient isolator that imposes minimal radiation interference on the other components and modules of the generator.

Figure 1:
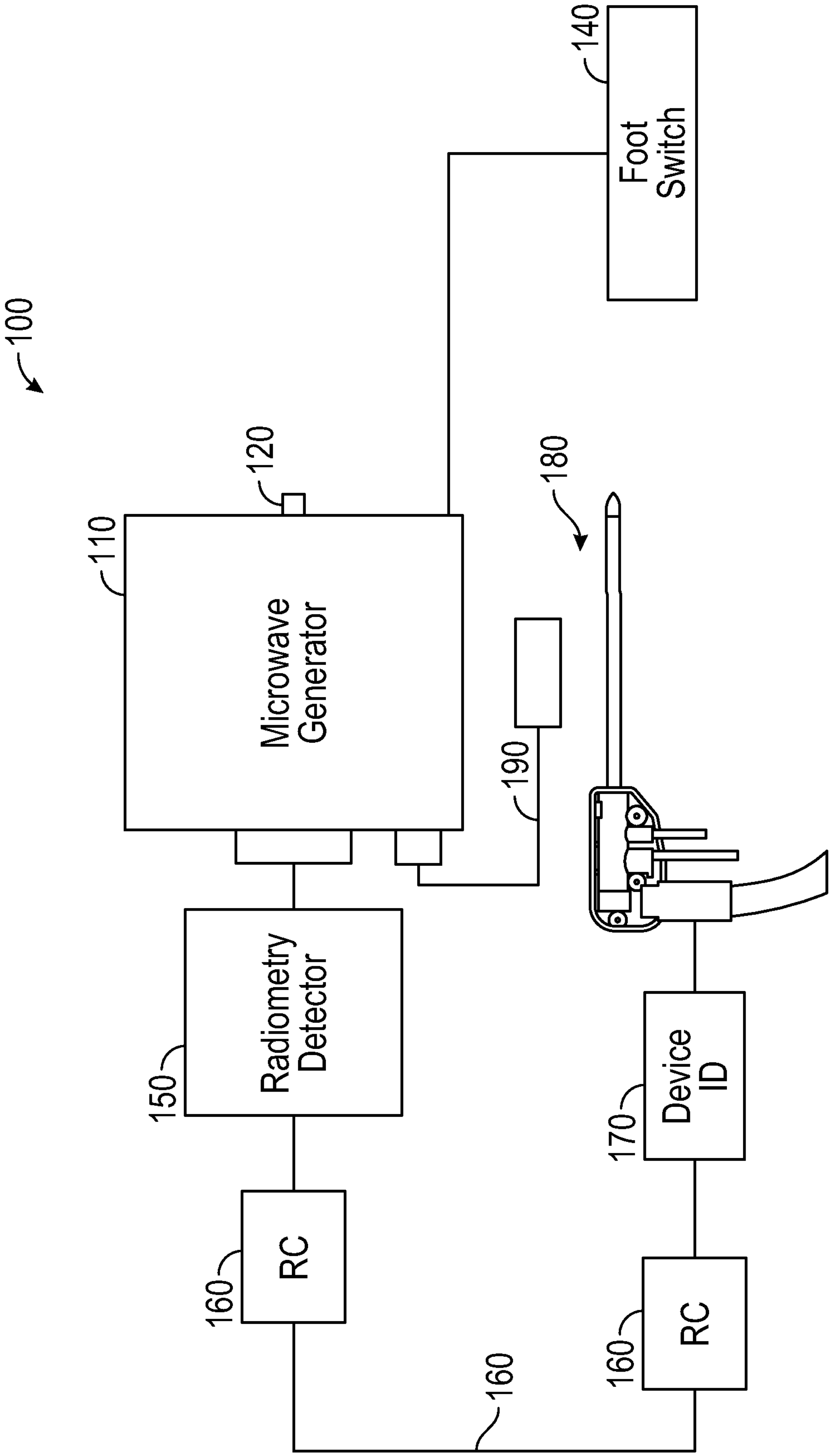
FIG. 1 is a block diagram of a microwave ablation system.

FIG. 1 is a block diagram of a microwave ablation system in accordance with embodiments of the present disclosure. As shown in FIG. 1, the microwave ablation system 100 generally includes a microwave generator 110, a connected device 180 (e.g., a microwave ablation instrument such as a microwave antenna) connected to the microwave generator 110 by a reusable cable 160, and a radiometer 150. The connected device 180 includes a device ID module 170 having a device unique identification resistor ("DUIR") 240 and a device ID memory 260 (see FIG. 2B). The DUIR 240 has a device unique identification ("DUID") resistance that may be measured by the microwave generator 110 and compared to a resistance value indicator stored in memory of the microwave generator 110 to identify a type of the connected device 180. Based on the identified type of the connected device 180, a determination can be made as to whether or not the connected device is of the type that is compatible with the microwave generator 110. The device ID module 170 may be incorporated within the connected device 180 or may be incorporated within a separate connector or adapter configured to mate with a connector of the reusable cable 160. Thus, the reusable cable 160 may connect to the DUIR 240 and to the device ID memory 260 via connection to the device 180, or the reusable cable 160 may connect to the DUIR 240 and to the device ID memory 260, which, in turn, connect to the device 180. Similar memories and/or resistors storing device-specific information may be included in the reusable cable 160 and the radiometer 150. The microwave generator 110 may also be connected to a footswitch 140 via a footswitch port on the microwave generator 110.

During the use of the microwave ablation system 100, a variety of different subsystems may be employed. Typically, the operation of the subsystems is controlled by a microprocessor-driven console (e.g., the microwave generator 110). The microprocessor receives mechanical inputs from the operator of the microwave ablation system 100 or from an assistant. A control input device, such as the footswitch 140, is used to accept mechanical inputs from the operator so that the operator can govern the operation of the subsystems within the microwave ablation system 100. When actuated by an operator, the control input device transmits electrical signals to the microprocessor control system. The electrical signals are then used to control the operational characteristics of a subsystem in the microwave ablation system 100.

As shown in FIG. 1, the microwave generator 110 is connected to a remote temperature probe 190. The remote temperature probe 190 may include a temperature sensor such as a thermocouple or a thermistor, and may include a memory storing a device ID or other information such as status information. The remote temperature probe 190 is operable to measure temperature of tissue at a surgical site. In one embodiment, the remote temperature probe 190 is configured to continuously output the temperature signal to the microwave generator 110 allowing a user to observe the temperature or to control the microwave generator 110 based on the temperature signal.

Figure 2A:
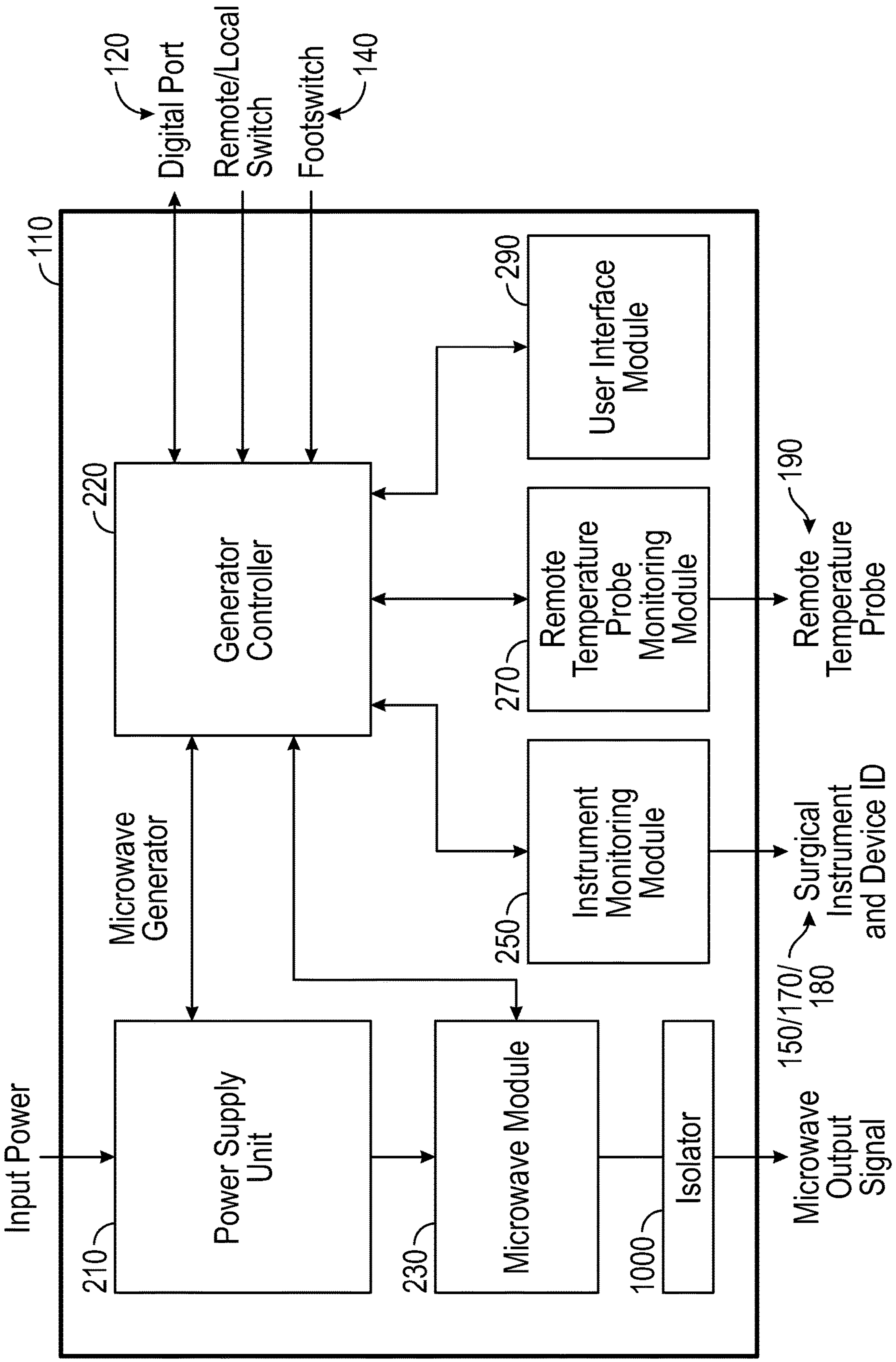
FIG. 2A is a circuit block diagram of the microwave generator of the microwave ablation system of FIG. 1.

FIG. 2A is a circuit block diagram of the microwave generator 110 of FIG. 1, which is configured to output microwave signals according to an embodiment of the present disclosure. Microwave generator 110 may include any of, a subset of, or all of a power supply module or unit 210, a generator control module or generator controller 220, a microwave module 230, an instrument monitoring module 250, a remote temperature probe monitoring module 270, a user interface module 290, and a patient isolator 1000.

The power supply unit 210 is electrically connected to the generator controller 220 and the microwave module 230 to supply power to the generator controller 220 and the microwave module 230. The generator controller 220, in turn, is electrically connected to the instrument monitoring module 250, the remote temperature probe monitoring module 270, and the user interface module 290 by electrical conductors, such as wires or traces, for supply power to the connected device 180 or instrument monitoring module 250, the remote temperature probe monitoring module 270, and the user interface module 290. The generator controller 220 is also in communication with the instrument monitoring module 250, the remote temperature probe monitoring module 270, and the user interface module 290 through a communications conduit such as the electrical conductors described above, optical fibers, or a wireless communications link.

In an embodiment of the present disclosure, any of, a subset of, or all of these modules may be removably connectable to ports or terminals of the microwave generator 110. For example, only the auxiliary modules, e.g., the instrument monitoring module 250, the remote temperature probe monitoring module 270, and the user interface module

290, may be removably connected to the microwave generator 110 and the other modules may be more permanently built into the microwave generator 110. A detailed description of a remote temperature probe monitoring module and a user interface module in accordance with embodiments of the present disclosure is provided in commonly-owned U.S. Patent Publication No. 2017/0333128 filed on May 18, 2017, the entire contents of which are incorporated herein by reference.

Microwave generator 110, as shown in FIG. 1, also includes digital port 120 that is configured to receive a connector to establish connections with a programming device or a device intended to communicate with individual components or modules of the microwave generator 110 (see FIG. 2A). The programming device, while connected to the digital port 120, may communicate and program the individual modules through the generator controller 220.

Figure 2B:
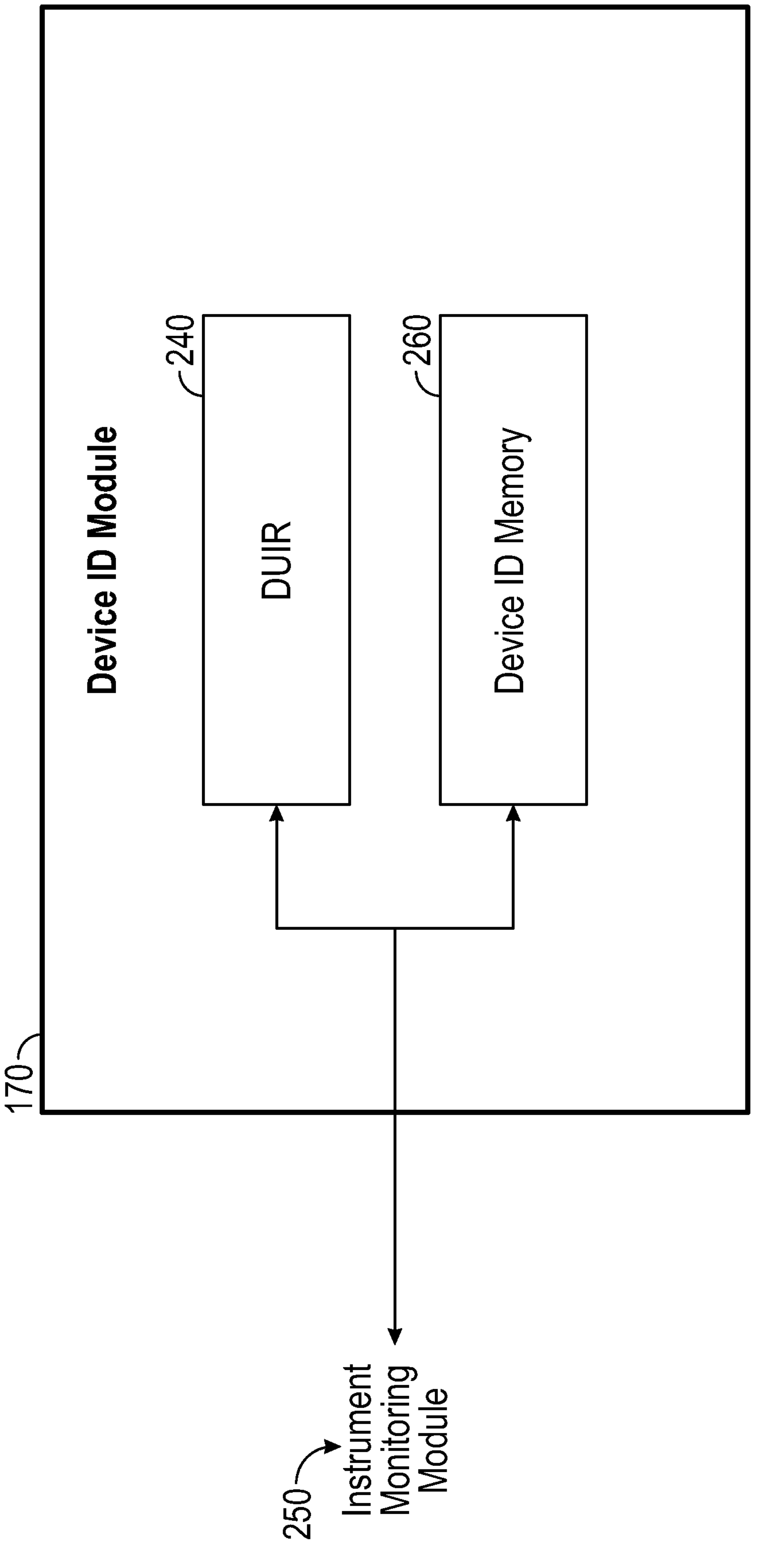
FIG. 2B is a block diagram of the microwave device of the microwave ablation system of FIG. 1.
Figure 3:
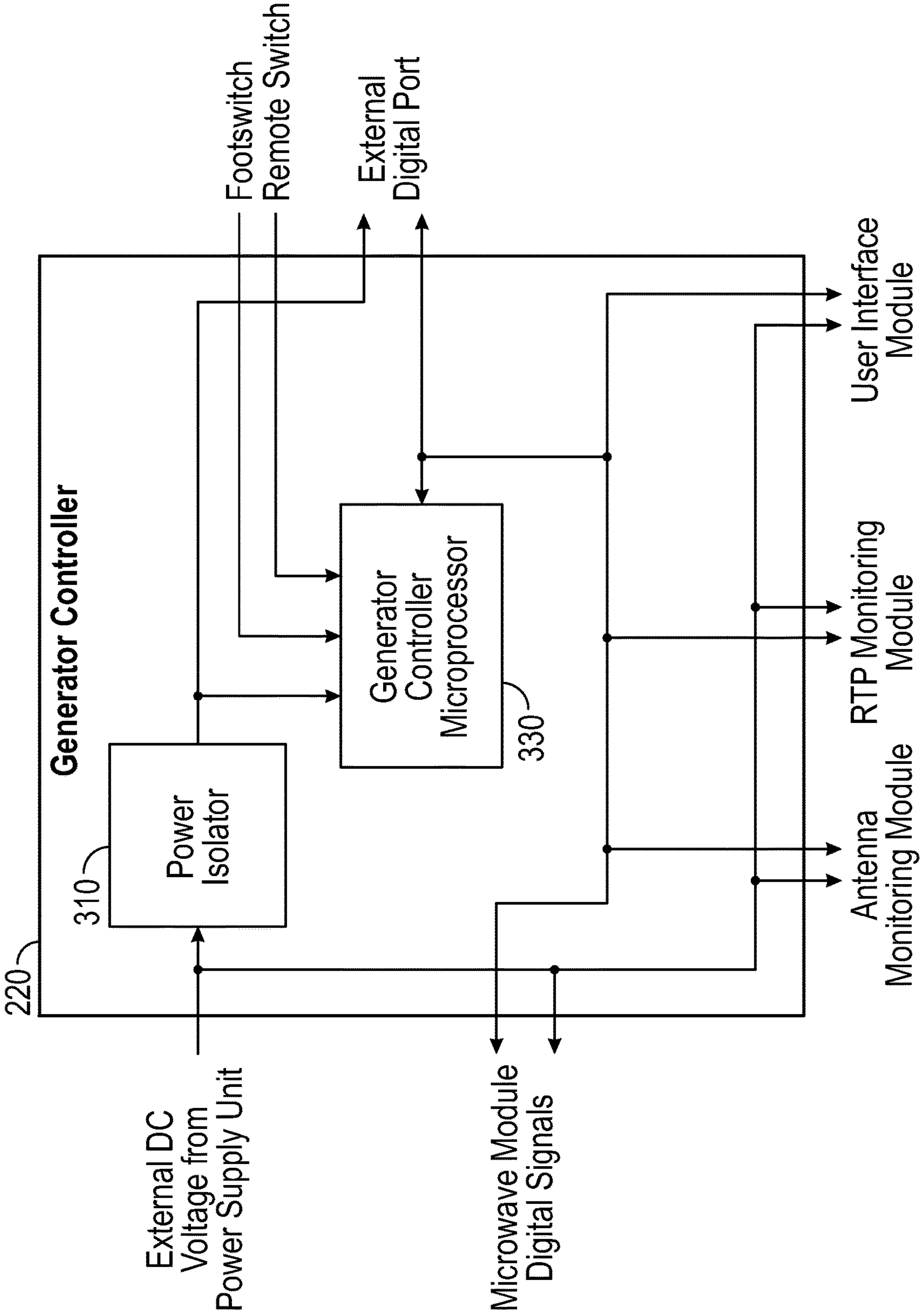
FIG. 3 is a circuit block diagram of a generator controller of the microwave generator of FIG. 2A.

FIG. 2B is a circuit block diagram of the device ID module 170 of FIG. 1 according to an embodiment of the present disclosure. Device ID module 170 includes the DUIR 240 and the device ID memory 260, each of which are configured to communicate with any one or more of the modules of the microwave generator (e.g., the instrument monitoring module 250) via the reusable cable 160. Upon startup and with a device connected to the microwave generator 110 via the reusable cable 160, the microwave generator 110 at any time as requested by the generator controller 220 or by a user may provide a precision current to the DUIR 240 via the reusable cable 160 to generate the DUID resistance value. The instrument monitoring module 250 measures the DUID resistance value and communicates this value to the generator controller 220. To identify the type of the connected device 180, the generator controller 220 processes the DUID resistance value received from the instrument monitoring module 250 and compares the processed DUID resistance value to a plurality of resistance value indicators stored in memory of the generator controller 220 that each correspond to a particular device type. The identified type of the connected device 180 may determine whether or not the connected device is compatible with the microwave generator 110. The type of a device may correspond to a particular capability of a device, a model of device, a particular series of a model of a device, a particular type of treatment modality of a device, whether or not a device is smart, a compatibility of a device with a microwave generator, or any combination of the foregoing. Device-specific operating thresholds for configuring operation of the microwave generator 110 for use with the connected device 180 may be determined based on the identified type of the connected device 180. An example of how device-specific operating thresholds for configuring microwave generator operation based on identified device type in accordance with embodiments of the present disclosure is provided in commonly-owned U.S. Provisional Patent Application No. 62/774,927, filed on Dec. 4, 2018, the entire contents of which are incorporated herein by reference FIG. 3 illustrates the generator controller 220 of the microwave generator 110 according to an embodiment of the present disclosure. The generator controller 220 includes a power isolator 310 that receives external DC voltage from the power supply unit 210. The power isolator 310 may include a transformer having a primary winding and a secondary winding. Power received by the power isolator 310 passes through the primary winding of the transformer, which induces a current in the secondary winding of the transformer proportional to the current received by the power isolator 310. The induced current provides power to a generator controller microprocessor 330. In an embodiment, the power isolator 310 supplies power to the generator controller microprocessor 330 at, for example, 12 VDC with a maximum power draw of 50 W. The generator controller microprocessor 330 also supplies 12 VDC to the generator subsystems, including the microwave module 230, the instrument monitoring module 250, the remote temperature probe monitoring module 270, and the user interface module 290.

The generator controller microprocessor 330 is a programmable processor configured through flash programming, or through other suitable programming methods and languages, to communicate digitally with the microwave module 230, the instrument monitoring module 250, the remote temperature probe monitoring module 270, the user interface module 290, the footswitch 140, other remote switches, and a device connected to the digital port 120 of the microwave generator 110. The generator controller microprocessor 330 may be calibrated through software calibration methods including radix-based digital self-calibration, background equivalent radix extraction, interference cancelling, or hardware calibration methods including the use of, for example, comparator/digital-to-analog converter (DAC) combinations, digitally controllable low-pass filters using a digital potentiometer, calibration-multiplexers, or any hardware and/or software solutions, to improve the digital communications links. As part of its communication with the microwave module 230, the instrument monitoring module 250, the remote temperature probe monitoring module 270, and the user interface module 290, the generator controller microprocessor 330 communicates information regarding the generator controller microprocessor 330 including, for example, status information, serial number, and firmware version to each component, while receiving, from each component, information regarding the generator controller microprocessor 330 including, for example, status information, serial number, and firmware version, which the generator controller microprocessor 330 continually processes and monitors.

The generator controller microprocessor 330 digitally communicates with the user interface module 290 to receive user inputs and send information that may be communicated to a user by the user interface module 290. The generator controller microprocessor 330 may issue a signal to the user interface module 290 causing the user interface module 290 to prompt a user to enter a microwave power level or a treatment time. Upon user selection, the user interface module 290 sends the generator controller microprocessor 330 a signal indicating the selection and the generator controller microprocessor 330 receives and processes the signal before issuing a signal to the microwave module 230 to set the power level or treatment time. In the alternative, the generator controller microprocessor 330 may delay a signal to the microwave module 230. For instance, if the generator controller microprocessor 330 receives a treatment time, the generator controller microprocessor 330 sends a signal to the microwave module 230 only when the allotted time has ended. While the treatment occurs, the generator controller microprocessor 330 counts down the selected treatment time. In addition to issuing an end signal to the microwave module 230, the generator controller microprocessor 330 communicates with the user interface module 290 throughout the countdown to send the user interface module 290 information regarding the remaining treatment to display including the remaining treatment time to indicate to a user how much time remains.

Figure 4:
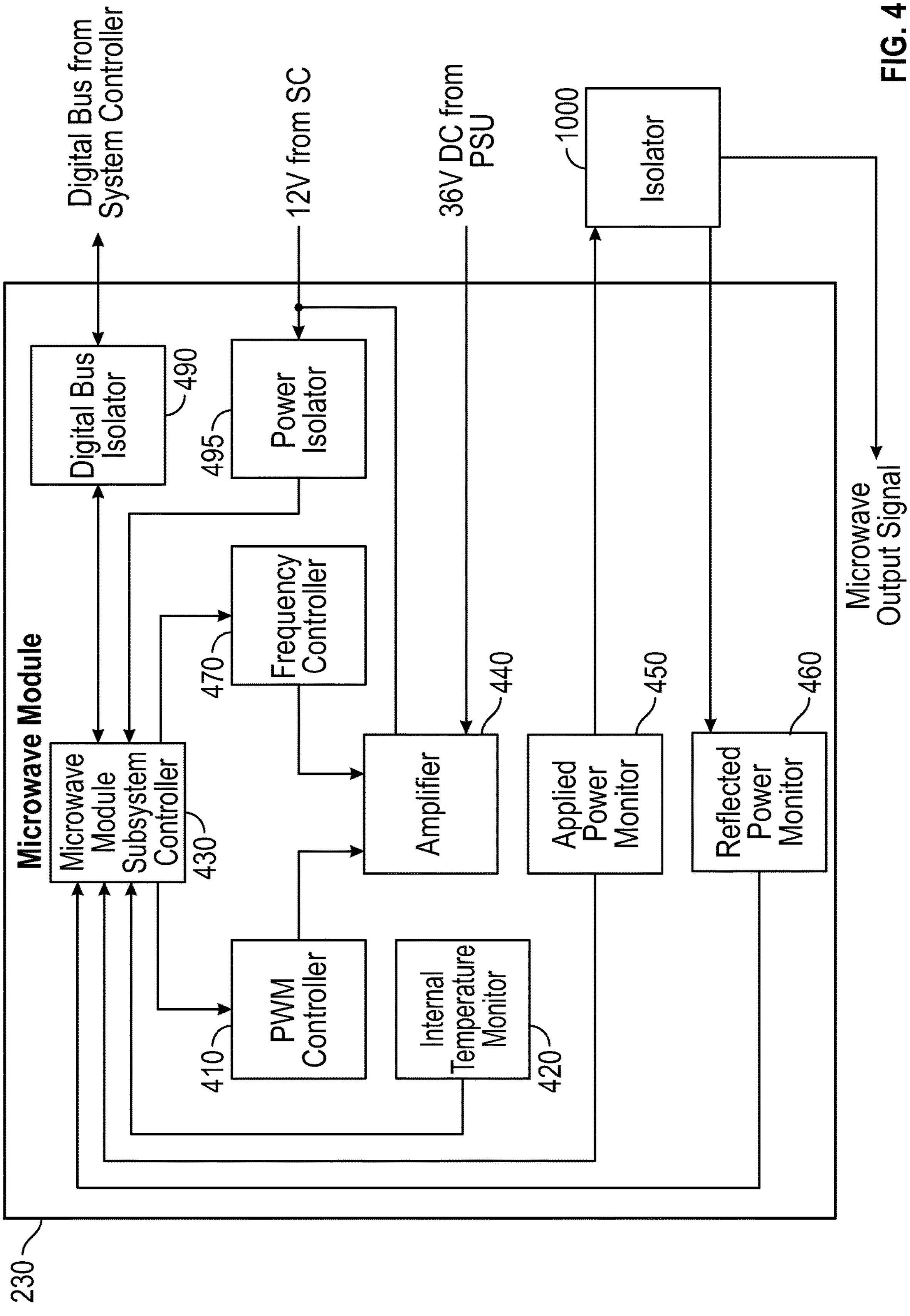
FIG. 4 is a circuit block diagram of a microwave module of the microwave generator of FIG. 2A.

FIG. 4 illustrates the microwave module 230 and patient isolator 1000 of the microwave generator 110 according to an embodiment of the present disclosure. The microwave module 230 contains various components including a Pulse Width Modulation (PWM) controller 410, an internal temperature monitor 420, a microwave module subsystem controller 430, an amplifier 440, an applied power monitor 450, a reflected power monitor 460, a digital bus isolator 490, and a power isolator 495. The microwave module subsystem controller 430 receives power, e.g., 12 VDC with a maximum power draw of 50 W, from the generator controller 220 through the power isolator 495. The power isolator 495 isolates the power supplied to the microwave module subsystem controller 430 from the generator controller 220.

The microwave module subsystem controller 430 is a programmable processor configured through flash programming, or through other suitable programming methods and languages, to produce up to, for example, 150 W, according to a setting set by a user, and maintain the power setting within, for example, a −5% to +20% range. The microwave module subsystem controller 430 is configured with interlock state settings pertaining to power, current, voltage, temperature, or any other measurable standard suitable for protecting the microwave module 230. If an interlock value is exceeded, the microwave module subsystem controller 430 may cease the supply of power to any or all components included in the microwave module 230.

Power is received by the power isolator 495 from the generator controller 220. The power isolator 495 is similar to the power isolator 310, which includes one or more transformers, one or more optocouplers, or other suitable circuitry for electrically isolating the microwave module 230 from the other modules and circuitry of the microwave ablation system 100. The power isolator 495 provides power to a microwave module subsystem controller 430. In some embodiments, the power isolator 495 may also provide power to the amplifier 440.

The internal temperature monitor 420 continually measures the temperature of the amplifier 440. The internal temperature monitor 420 may employ a thermocouple, a thermistor, or other suitable temperature sensor. The internal temperature monitor 420 further transmits temperature data to the microwave module subsystem controller 430. The microwave module subsystem controller 430 routes the amplifier 440 temperature data through the digital bus isolator 490 to the generator controller 220 as a value in, for example, degrees Celsius. While monitoring temperature of the amplifier 440, the internal temperature monitor 420 may cause a cooling system to redistribute and remove heat generated by the amplifier 440.

The PWM controller 410 generates a pulse width controlled power signal according to instructions from the microwave module subsystem controller 430. The frequency controller 470 generates a frequency controlled power signal according to instructions from the microwave module subsystem controller 430. The amplifier 440 receives a Pulse Width Modulation (PWM) signal from the PWM controller 410, a frequency control signal from the frequency controller 470, and power, e.g., 36 VDC with a maximum power draw of 350 W, from the power supply unit 210. Using the power from the power supply unit, the amplifier 440 amplifies the PWM signal and changes the frequency of the PWM signal according to the frequency control signal to produce a microwave signal. The power signal is provided to the patient isolator 1000 through the applied power monitor 450. The applied power monitor 450 determines the power, voltage, current, and waveform of the microwave signal and communicates the information with the microwave module subsystem controller 430 to allow the microwave module subsystem controller 430 to recalibrate the microwave signal.

At the patient isolator 1000, the patient is electrically isolated from the microwave module 230 power source. The patient isolator 1000 outputs a microwave signal to the connected device 180 and isolates the connected device 180 and patient from the remaining components of the microwave module 230 and other components and modules of the microwave generator 110. The patient isolator 1000 is described in greater detail below with respect to FIGS. 6A-6C and 7.

The reflected power monitor 460 is connected to the patient isolator 1000 and monitors the reflected return signal. The reflected power monitor 460 can measure voltage, current, power, and/or impedance. Information determined at the reflected power monitor 460 is communicated with the microwave module subsystem controller 430, where it allows the microwave module subsystem controller 430 to calibrate the microwave signal. The microwave module subsystem controller 430 may compare information from reflected power monitor 460 and applied power monitor 450 to determine the loss and phase shift between incident and reflected waves of the microwave signal. Additionally, the microwave module subsystem controller 430 may communicate raw data or processed data through the digital bus isolator 490, which is configured, using a transformer or other isolation device, to electrically isolate the microwave module subsystem controller 430 from other modules connected to the digital bus.

Figure 5:
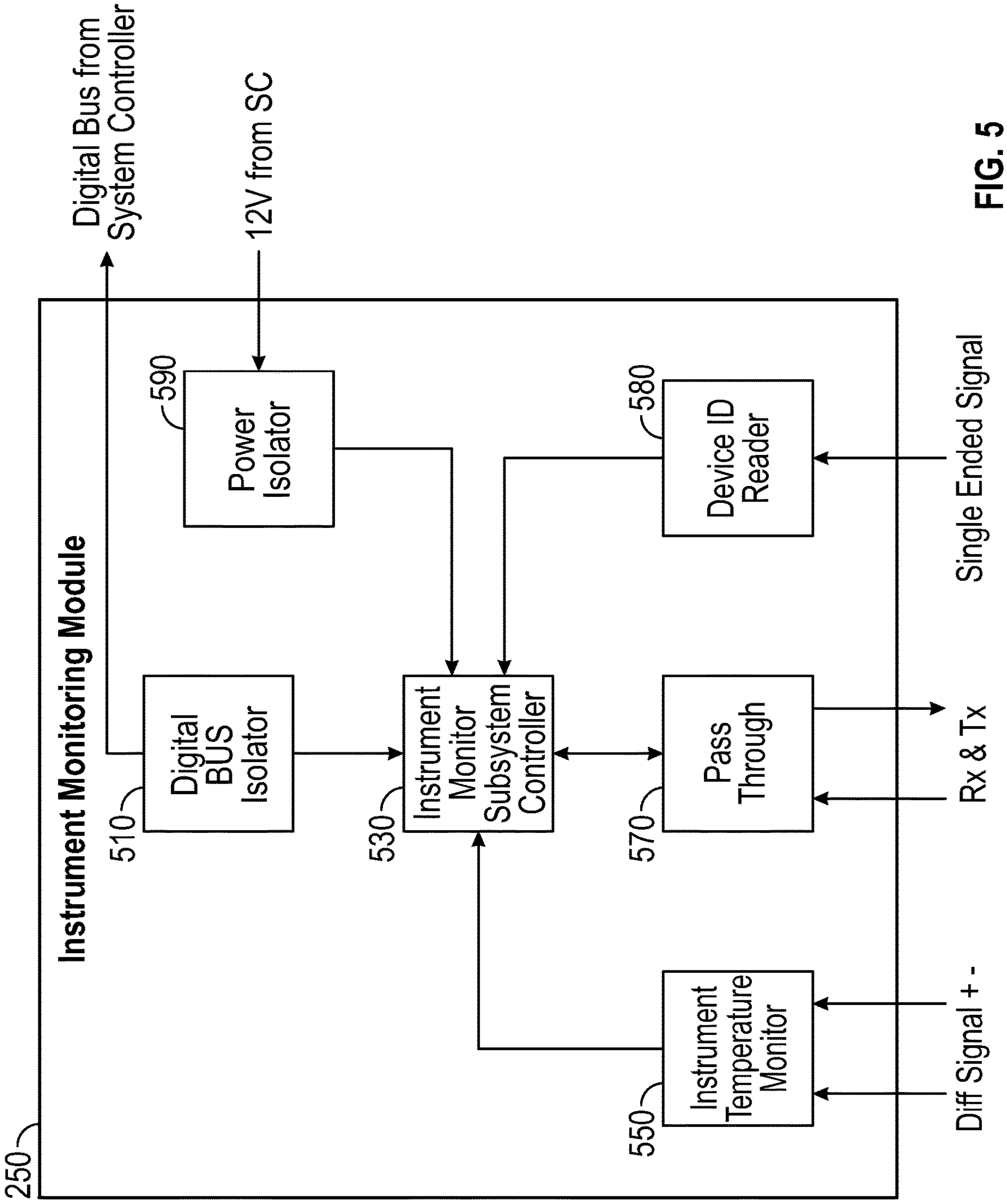
FIG. 5 is a circuit block diagram of an instrument monitoring module of the microwave generator of FIG. 2A.

FIG. 5 is a circuit block diagram of the instrument monitoring module 250 of the microwave generator 110 according to an embodiment of the present disclosure. The instrument monitoring module 250 includes a digital bus isolator 510, a power isolator 590, an instrument monitoring subsystem controller 530, an instrument temperature monitor 550, a pass through circuit 570, and a device ID reader 580. The power isolator 590 is similar to the power isolator 310, which includes one or more transformers, one or more optocouplers, or other suitable circuitry for electrically isolating the user interface module 290 from the other modules and circuitry of the microwave ablation system 100. The power isolator 590 provides power to the instrument monitor subsystem controller 530.

The instrument monitor subsystem controller 530 controls and communicates with the instrument temperature monitor 550, the pass through circuit 570, and the device ID reader 580. The instrument monitor subsystem controller 530 also communicates with the generator controller 220 through a digital bus connected to the digital bus isolator 510, which relays a communication signal while electrically isolating the instrument monitor subsystem controller 530.

Upon startup or at any time as requested by the generator controller 220 or by a user, the generator controller 220 may instruct the device ID reader 580 to measure the DUID resistance of the connected device 180 and communicate the measured DUID resistance value to the instrument monitor subsystem controller 530 for processing and communication to the generator controller 220. If the connected device 180 is identified as a smart device based on the measured DUID resistance of the connected device 180, the generator controller 220 may instruct the instrument monitor subsystem controller 530 to pass request data packets to the device ID memory 260 of the connected device 180 via the reusable cable 160. Upon receipt of the request data packet from the instrument monitor subsystem controller 530, the device ID memory 260 of the connected device 180 responds to the instrument monitor subsystem controller 530 by communicating the requested data packet including device-specific data to the instrument monitor subsystem controller 530 via the device ID reader 580. Device ID reader 580 may receive a single-ended signal including the requested data packet, which is then communicated to instrument monitor subsystem controller 530 for processing and communication to generator controller 220.

Upon starting a procedure, the instrument monitor subsystem controller 530 instructs the instrument temperature monitor 550 to begin monitoring a temperature of the connected device 180. The instrument temperature monitor 550 determines a voltage differential across two lines connected with, for example, a thermocouple or thermistor, to determine a temperature of the connected device 180.

The pass through circuit 570 receives a digital signals through the receive (Rx) channel and outputs the digital signals through the transmit (Tx) channel. The pass through circuit 570 allows the instrument monitor subsystem controller 530 to communicate with the connected device 180. The instrument monitor subsystem controller 530 analyzes the data and transmits the information to the generator controller 220 via the digital bus and the digital bus isolator 510.

Figure 6A:
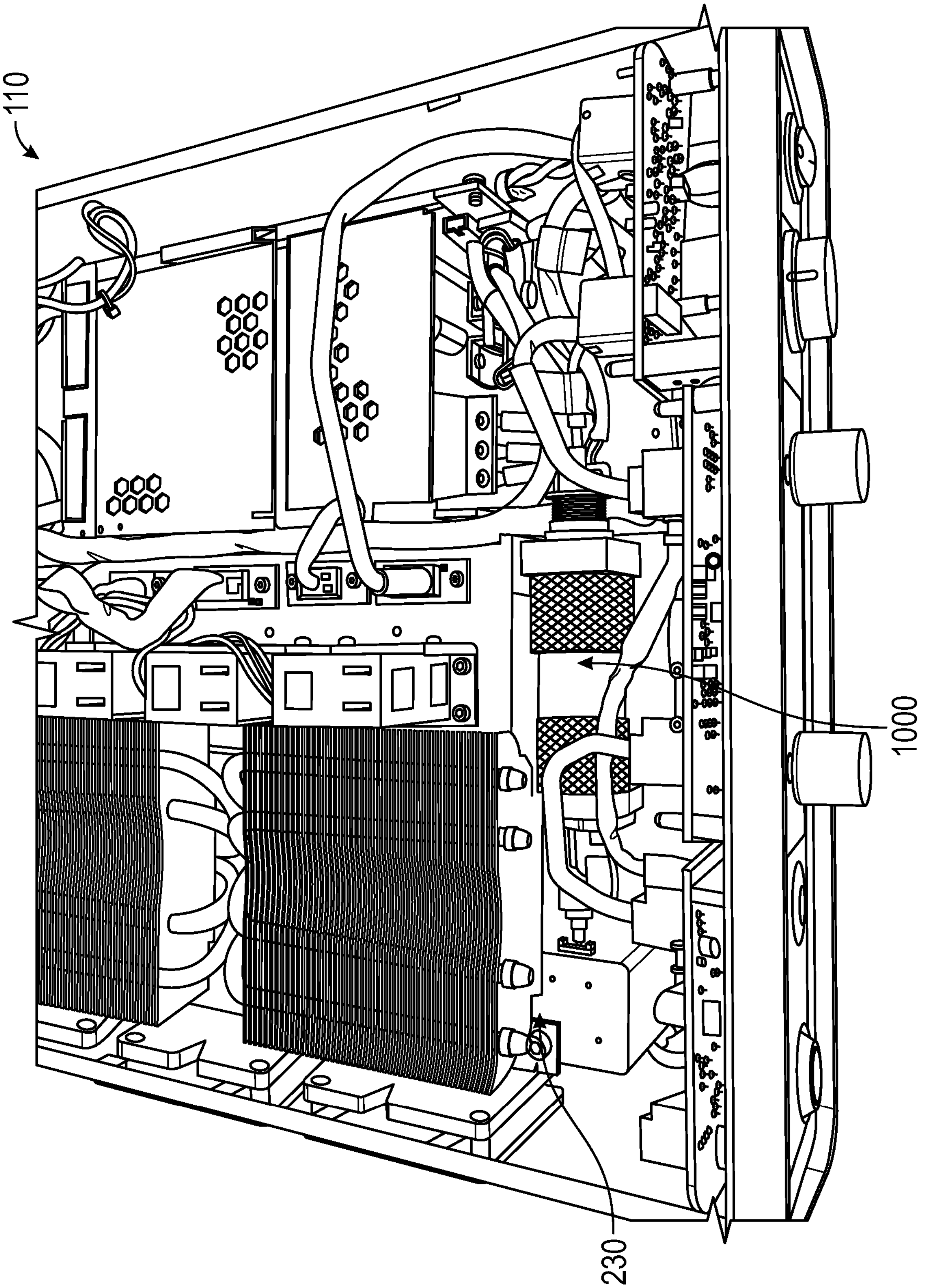
FIG. 6A is a perspective view of a generator including a patient isolator coupled to a microwave module of the microwave generator of FIG. 2A.
Figure 6B:
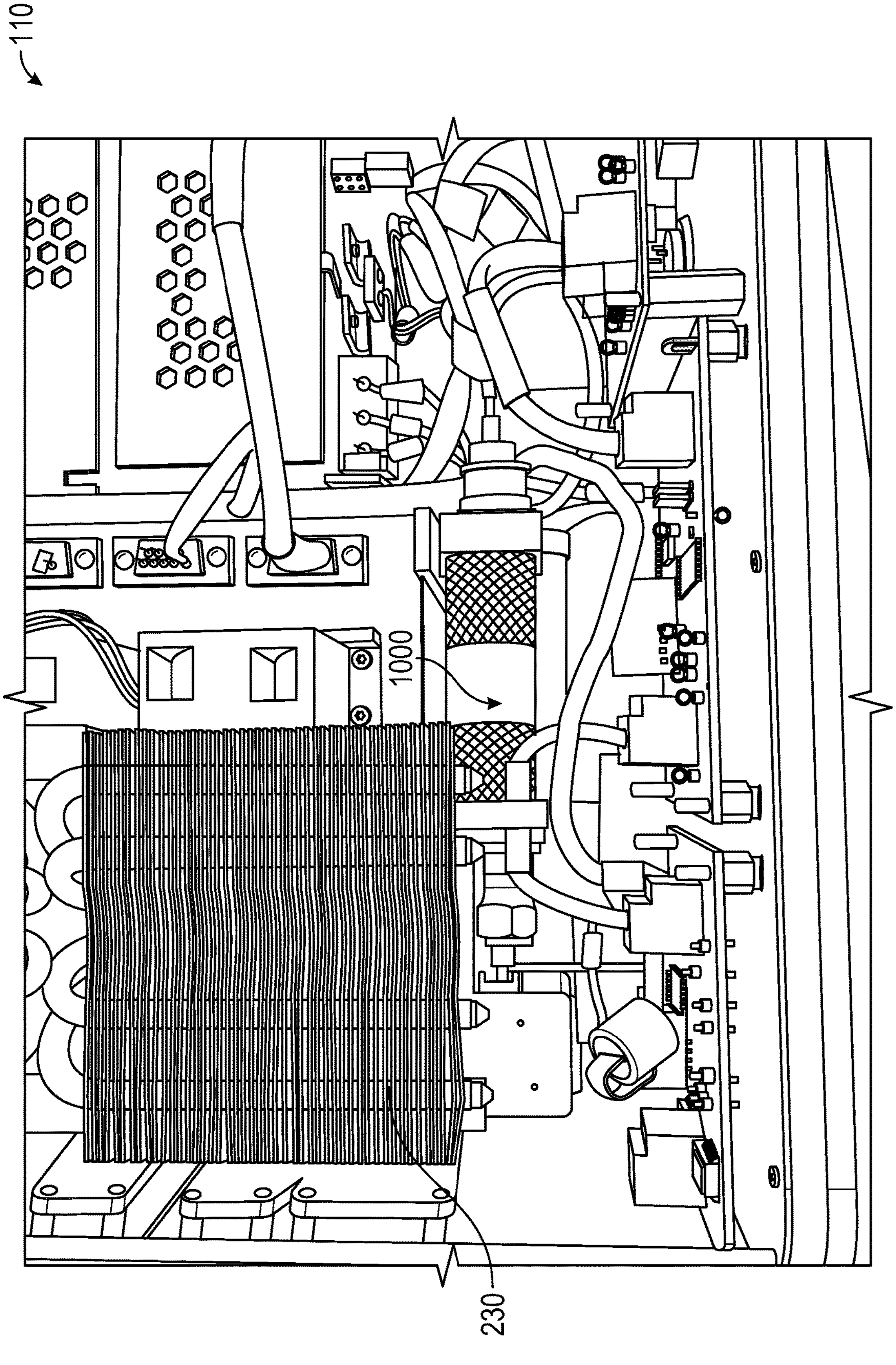
FIG. 6B is a top view of a generator including a patient isolator coupled to a microwave module of the microwave generator of FIG. 2A.
Figure 6C:
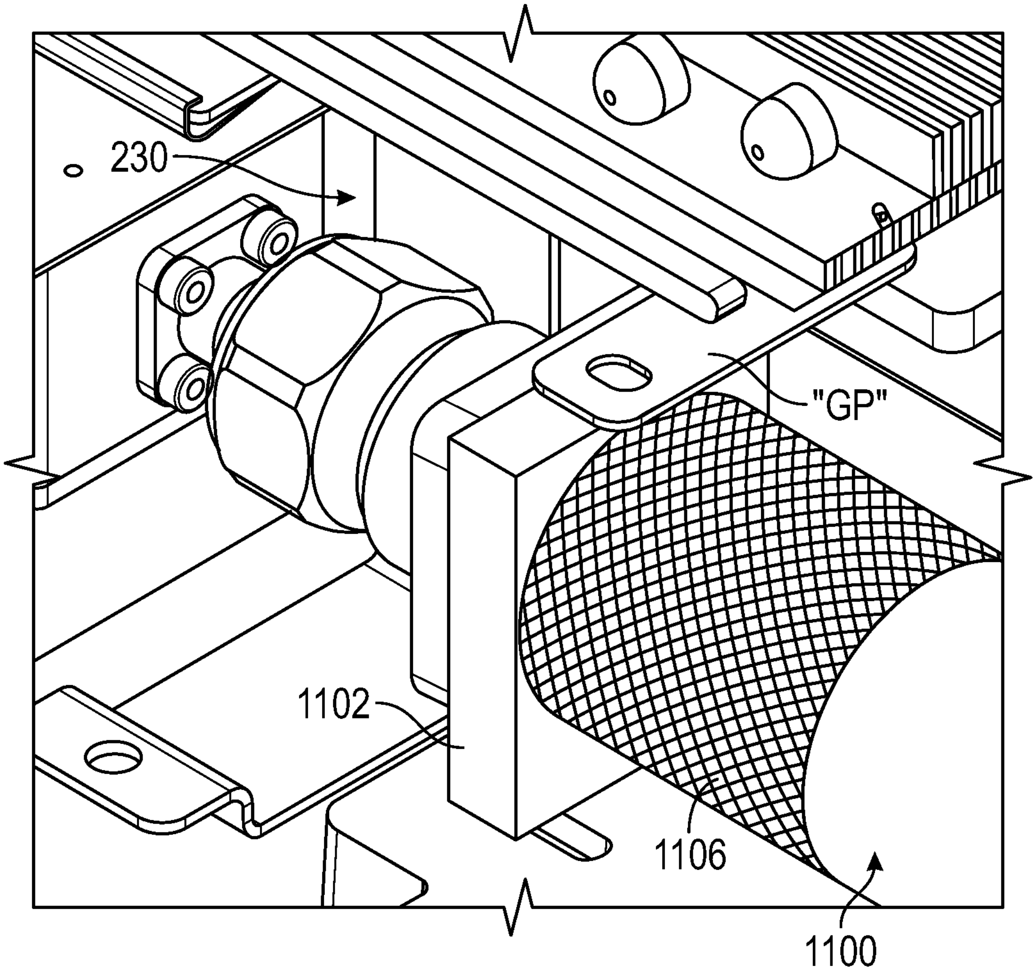
FIG. 6C is a perspective view of a patient isolator grounded to a microwave module of the microwave generator of FIG. 2A.
Figure 7:
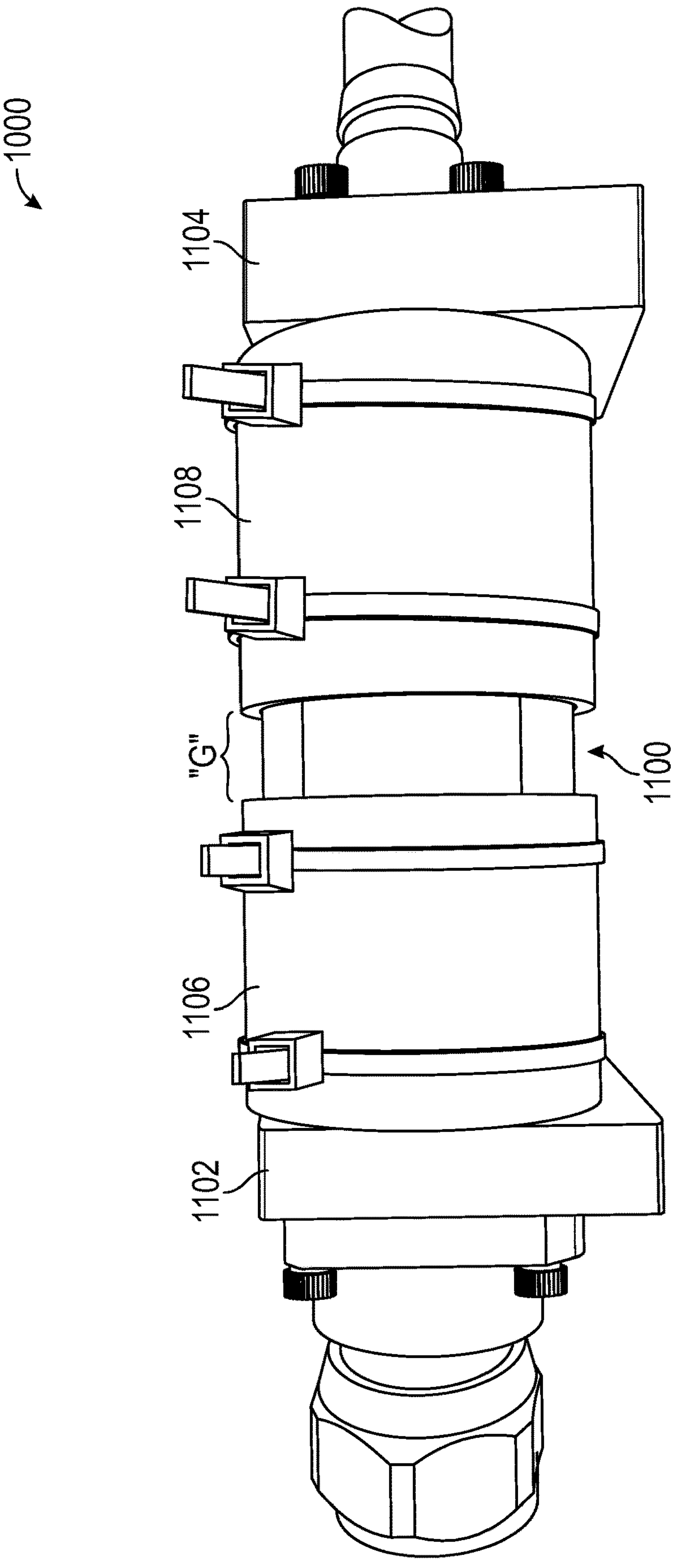
FIG. 7 is a perspective view of a patient isolator of the microwave generator of FIG. 2A.

FIGS. 6A-6C illustrate the patient isolator 1000 connected to the microwave module 230. The patient isolator 1000 shown in FIGS. 6A-6C and 7 includes a high loss cavity resonance absorber split in two parts, each of which is wrapped around a portion of a DC block 1100. The DC block 1100 is grounded to the microwave module 230. Such an arrangement has proven effective in reducing the amount of unwanted radiation emitted from the DC block 1100 and, in particular, interference imparted onto signals associated with the remote temperature probe 190 measurements. Specifically, the remote temperature probe 190 measurement signals are particularly prone to interference generated by DC block patient isolators during activation and delivery of microwave energy. DC block patient isolators operate with capacitive gaps across breaks in the inner and outer conductors of the coaxial waveguide. Low frequency signals see this coupling as high impedance, whereas the operational frequency of 2.45 GHz sees this coupling as low impedance. However, the breaks in the outer conductor of the coaxial line within the DC block allow for unwanted and interfering radiation of high frequency energy outside the waveguide, thereby causing interference to other components of the microwave generator 110. In one example, the second harmonic (~4.9 GHz) of the operating frequency radiates from the DC block into the generator chassis and out of the chassis into free space.

Figure 8:
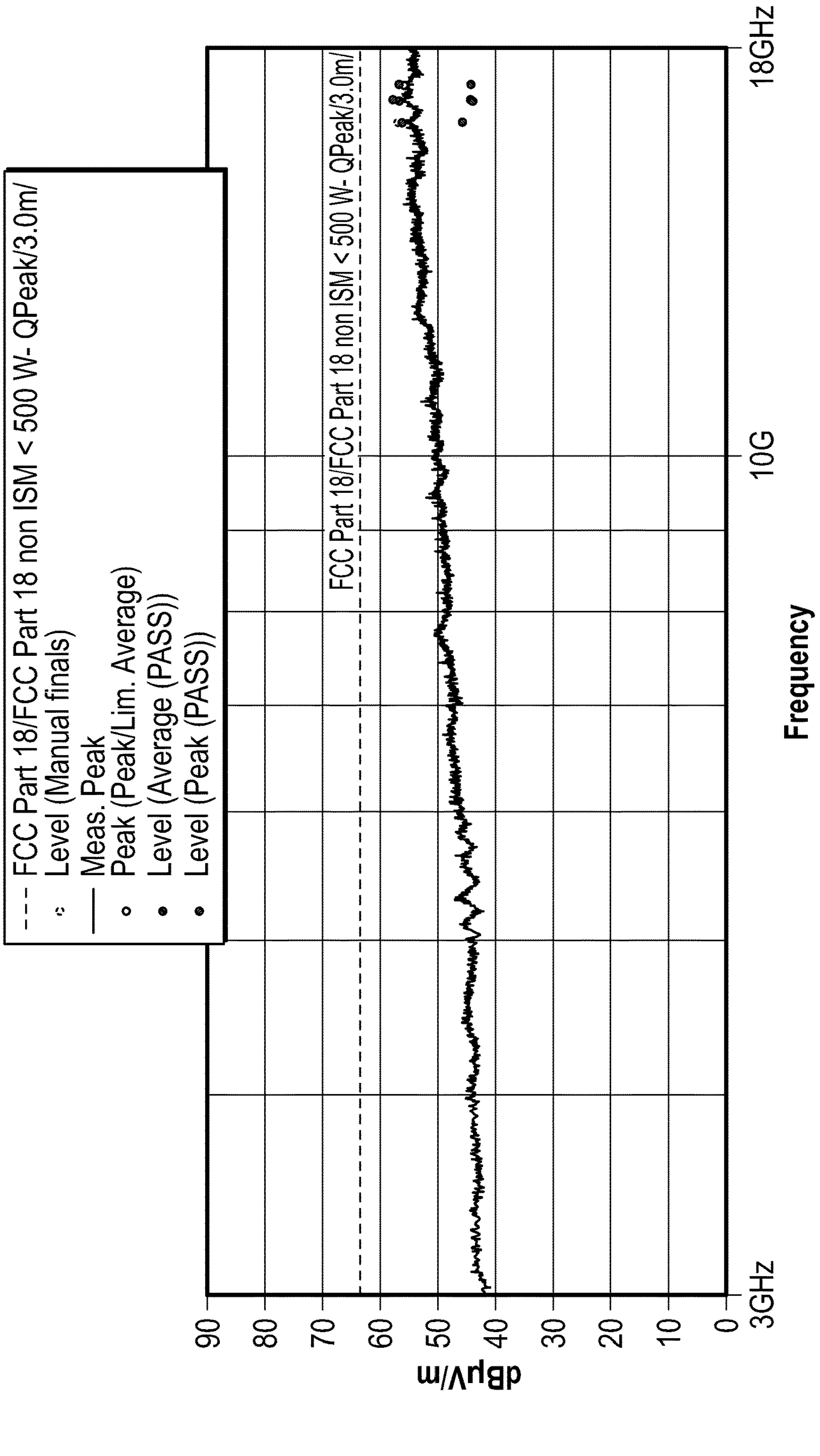
FIG. 8 is a graph illustrating experimental results of radiated emissions and FCC part 18 limits.

The accuracy of sensor measurements is reduced as the output of microwave energy is increased due to the interference imparted thereon by the radiation emitted from the patient isolator. The accuracy of the sensor measurements ensures the successful operation of the microwave generator 110. For example, the accuracy of the remote temperature probe 190 readings is reduced as the output of microwave energy is increased due to the interference imparted thereon by the radiation emitted by the patient isolator. The accuracy of the remote temperature probe 190 readings ensures successful operation of the microwave generator 110 and patient safety. Accordingly, the presently described systems ensure that the measurements provided by sensors, for example sensors of the remote temperature probe 190, are accurate and not interfered with by radiation produced by other components of the system. Inaccurate sensor data compromises the control and output of the microwave generator 110. Additionally, there are radiation limits set by regulating bodies (e.g., FCC rules 47 CFR Part 18) which were not met without the improvements detailed herein. Referring briefly to FIG. 8, a graph is illustrated reflecting the experimental data of radiated emissions using the discloses patient isolator falling below the FCC standards.

Grounding a patient isolator to the microwave module 230 has proven to only slightly reduce the interference imparted on the remote temperature probe 190 measurement signal by the grounded patient isolator. Similarly, wrapping a patient isolator with a high loss cavity resonance absorber along its length has proven to only slightly reduce the interference imparted on the remote temperature probe 190 measurement signal by the wrapped patient isolator. Even further, both grounding a patient isolator and wrapping the grounded patient isolator with a high loss cavity resonance absorber along its length has also proven to only slightly reduce the interference imparted on the remote temperature probe 190 measurement signal by the grounded and wrapped patient isolator. Such a slight reduction in the interference, as achieved by the above-described designs, is insufficient for obtaining an accurate remote temperature probe 190 measurement. However, the combination of grounding the patient isolator to the microwave module 230 and wrapping a proximal portion of the patient isolator with a high loss cavity resonance absorber and wrapping a distal portion of the patient isolator with a high loss cavity resonance absorber, with a gap between the two portions, in accordance with the present disclosure has been found to effectively reduce the interference imparted on the remote temperature probe 190 signals.

In particular, the embodiment of the split absorber described above, with a 6 mm gap present between the two portions of the absorber, has demonstrated a −9 dB improvement in radiation at 4.9 GHz in comparison to a mere −5 dB improvement in radiation utilizing a single centrally located absorber. Additionally, experimentation has also revealed that grounding of the patient isolator or microwave amplifier alone does not effectively reduce the radiation causing the interference, but that grounding of a proximal portion of the DC block itself effectively reduces radiation of a 6 cm wavelength at 4.9 GHz. In particular, use of a ground plate placed connecting a proximal portion of the DC block, the microwave amplifier, and the chassis of the microwave generator effectively reduces radiation of a 6 cm wavelength at 4.9 GHz.

As shown in FIGS. 6A-6C and 7, the patient isolator 1000 includes a DC block 1100, a proximal mounting block 1102, a distal mounting block 1104, a proximal absorber 1106, and a distal absorber 1108. A proximal end of the DC block 1100 is coupled to an output of the microwave module 230 and a distal end of the DC block 1100 is coupled to an output port for coupling the microwave generator to a connected device 180 (FIG. 1). At least one of the proximal mounting block 1102 or distal mounting block 1104 is formed of a conductive material (e.g., aluminum) and is grounded to a portion of the microwave module 230. In an embodiment, the proximal mounting block 1102 is grounded to the microwave module 230 via a ground plate "GP" (FIG. 6C) and the microwave module 230 is grounded to the chassis of the microwave generator 110.

DC block 1100 may operate with capacitive gaps across breaks in inner and outer conductors of a coaxial waveguide. Low frequency signals see this coupling as high impedance, whereas an operational frequency of 2.45 GHz sees this coupling as low impedance. The DC block 1100 is configured to isolate the patient from other components of the microwave generator 110.

The proximal absorber 1106 is wrapped around a proximal portion of the DC block 1100 and the distal absorber 1108 is wrapped around a distal portion of the DC block 1100. The proximal absorber 1106 is spaced apart from the distal absorber 1108 such that a gap "G" (FIG. 7) exists between the proximal absorber 1106 and the distal absorber 1108. In an aspect, the gap "G" is a 6 mm gap, but other gap distances are also contemplated. It has been found that grounding the proximal mounting block 1102 to the microwave module 230 and forming a gap distance of 6 mm between the proximal absorber 1106 and the distal absorber 1108 provides excellent attenuation of interference radiation. At least one of the proximal absorber 1106 or the distal absorber 1108 may be a high loss cavity resonance absorber. In an aspect, at least one of the proximal absorber 1106 or the distal absorber 1108 is a thin magnetically loaded sheet stock having loss at microwave frequencies, while maintaining the desirable characteristics of elastomeric binders. The proximal absorber 1106 or the distal absorber 1108 may be designed to exhibit high magnetic loss and attenuate energy at normal and high angles of incidence at frequencies from 1 GHz to 18 GHz. In one aspect, the elastomer of the proximal absorber 1106 or the distal absorber 1108 is silicone, but other elastomer formulations are contemplated.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A patient isolator for a microwave generator, the patient isolator comprising:
- a DC block configured to be grounded to a microwave module of a microwave generator;
- a proximal absorber wrapped around a proximal portion of the DC block;
- a distal absorber wrapped around a distal portion of the DC block and separated from the proximal absorber by a gap, wherein at least one of the proximal absorber or the distal absorber is a high-loss cavity resonance absorber; and
- a proximal mounting block and a distal mounting block, the proximal and distal mounting blocks configured to mount the DC block within the microwave generator, at least one of the proximal or distal mounting blocks being electrically conductive and configured to ground the DC block to the microwave module, wherein a proximal end of the proximal absorber contacts the proximal mounting block and a distal end of the distal absorber contacts the distal mounting block.

2. The patient isolator according to claim 1, wherein the gap separating the proximal and distal absorbers is about 6 mm.

3. The patient isolator according to claim 1, wherein the gap separating the proximal and distal absorbers is 6 mm.

4. A microwave generator, comprising:
- a microwave module configured to deliver a microwave signal to a microwave instrument coupled to the microwave generator;
- a generator controller in communication with the microwave module and configured to control the microwave module; and
- a patient isolator coupled to the microwave module, the patient isolator including:
  - a DC block grounded to the microwave module;
  - a proximal absorber wrapped around a proximal portion of the DC block;
  - a distal absorber wrapped around a distal portion of the DC block and separated from the proximal absorber by a gap, wherein at least one of the proximal absorber or the distal absorber is a high-loss cavity resonance absorber; and
  - a proximal mounting block and a distal mounting block, the proximal and distal mounting blocks configured to mount the DC block within the microwave generator, at least one of the proximal or distal mounting blocks being electrically conductive and configured to ground the DC block to the microwave module, wherein a proximal end of the proximal absorber contacts the proximal mounting block and a distal end of the distal absorber contacts the distal mounting block.

5. The microwave generator according to claim 4, wherein the gap separating the proximal and distal absorbers is about 6 mm.

6. The microwave generator according to claim 5, wherein the gap separating the proximal and distal absorbers is 6 mm.

7. A microwave ablation system comprising:
- a microwave instrument configured to deliver microwave energy to tissue; and
- a microwave generator configured to operably couple to the microwave instrument, the microwave generator including:
  - a microwave module configured to deliver a microwave signal to the microwave instrument;
  - a generator controller in communication with the microwave module; and
  - a patient isolator coupled to the microwave module, the patient isolator including:
    - a DC block grounded to the microwave module;
    - a proximal absorber wrapped around a proximal portion of the DC block;
    - a distal absorber wrapped around a distal portion of the DC block and separated from the proximal absorber by a gap, wherein at least one of the proximal absorber or the distal absorber is a high-loss cavity resonance absorber; and
  - a proximal mounting block and a distal mounting block, the proximal and distal mounting blocks configured to mount the DC block within the microwave generator, at least one of the proximal or distal mounting blocks being electrically conductive and configured to ground the DC block to the microwave module, wherein a proximal end of the proximal absorber contacts the proximal mounting block and a distal end of the distal absorber contacts the distal mounting block.

8. The microwave ablation system according to claim 7, wherein the gap separating the proximal and distal absorbers is about 6 mm.

9. The microwave ablation system according to claim 8, wherein the gap separating the proximal and distal absorbers is 6 mm.

* * * * *